(12) United States Patent
Fearon et al.

(10) Patent No.: US 8,688,416 B2
(45) Date of Patent: Apr. 1, 2014

(54) METHODS AND SYSTEMS FOR IMPROVED PHARMACEUTICAL INTERVENTION IN COAGULATION CONTROL

(76) Inventors: Michael Fearon, Annapolis Royal (CA); Paul Wegener, New York, NY (US)

( * ) Notice: Subject to any disclaimer, the term of this patent is extended or adjusted under 35 U.S.C. 154(b) by 194 days.

(21) Appl. No.: 13/123,774

(22) PCT Filed: Oct. 15, 2009

(86) PCT No.: PCT/US2009/060778
§ 371 (c)(1),
(2), (4) Date: Jun. 24, 2011

(87) PCT Pub. No.: WO2010/048020
PCT Pub. Date: Apr. 29, 2010

(65) Prior Publication Data
US 2011/0251834 A1 Oct. 13, 2011

Related U.S. Application Data

(60) Provisional application No. 61/106,695, filed on Oct. 20, 2008.

(51) Int. Cl.
*G06F 17/50* (2006.01)
*G06F 7/60* (2006.01)
*G06G 7/48* (2006.01)
*G06G 7/58* (2006.01)

(52) U.S. Cl.
USPC ............. 703/2; 703/1; 703/6; 703/11; 703/12

(58) Field of Classification Search
None
See application file for complete search history.

(56) References Cited

U.S. PATENT DOCUMENTS

| | | | | |
|---|---|---|---|---|
| 5,517,405 A | * | 5/1996 | McAndrew et al. | 706/45 |
| 5,594,638 A | * | 1/1997 | Iliff | 705/3 |
| 5,660,176 A | * | 8/1997 | Iliff | 600/300 |
| 5,672,154 A | * | 9/1997 | Sillen et al. | 604/503 |
| 5,833,599 A | * | 11/1998 | Schrier et al. | 600/300 |
| 5,845,255 A | * | 12/1998 | Mayaud | 705/3 |
| 5,908,383 A | * | 6/1999 | Brynjestad | 600/300 |
| 5,950,630 A | * | 9/1999 | Portwood et al. | 128/897 |
| 5,989,844 A | * | 11/1999 | Shimada et al. | 435/25 |
| 6,081,786 A | * | 6/2000 | Barry et al. | 705/3 |
| 6,188,988 B1 | * | 2/2001 | Barry et al. | 705/3 |
| 6,450,956 B1 | * | 9/2002 | Rappaport et al. | 600/300 |
| 6,584,445 B2 | * | 6/2003 | Papageorge | 705/3 |
| 6,687,685 B1 | * | 2/2004 | Sadeghi et al. | 706/15 |
| 6,871,171 B1 | * | 3/2005 | Agur et al. | 703/11 |
| 6,931,326 B1 | * | 8/2005 | Judson et al. | 702/20 |
| 6,942,614 B1 | * | 9/2005 | Kutzko et al. | 600/300 |

(Continued)

FOREIGN PATENT DOCUMENTS

| | | |
|---|---|---|
| CA | 2396262 | 7/2001 |
| WO | 01/50950 | 7/2001 |

(Continued)

*Primary Examiner* — Shambhavi Patel
(74) *Attorney, Agent, or Firm* — Fish & Associates, PC

(57) ABSTRACT

Contemplated methods and devices for coagulation control allow to establish a more constant dosage of required medication and to quantify/take into account patient-specific sensitivity to warfarin and Vitamin K by using logit (1/INR) as the dependent variable to so stabilize the variance across all values of INR. Moreover, it should be noted that such use simplifies the relation between INR and dose of coumarins or Vitamin K and reduces the number of parameters to be estimated for each patient.

15 Claims, 5 Drawing Sheets

(56) References Cited

U.S. PATENT DOCUMENTS

| | | | |
|---|---|---|---|
| 6,980,958 B1* | 12/2005 | Surwit et al. | 705/2 |
| 7,275,220 B2* | 9/2007 | Brummel et al. | 715/804 |
| 7,297,111 B2* | 11/2007 | Iliff | 600/300 |
| 7,433,828 B2* | 10/2008 | Brinkman et al. | 705/3 |
| 7,809,585 B1* | 10/2010 | Ghouri | 705/3 |
| 8,032,394 B1* | 10/2011 | Ghouri | 705/2 |
| 8,084,210 B2* | 12/2011 | Gladding et al. | 435/6.11 |
| 2002/0116222 A1* | 8/2002 | Wurster | 705/2 |
| 2004/0006337 A1* | 1/2004 | Nasab et al. | 606/41 |
| 2004/0084867 A1* | 5/2004 | Leyland-Jones | 280/163 |
| 2004/0193446 A1* | 9/2004 | Mayer et al. | 705/2 |
| 2004/0199333 A1* | 10/2004 | Hoffman et al. | 702/20 |
| 2004/0260478 A1 | 12/2004 | Schwamm | |
| 2005/0010206 A1* | 1/2005 | Nasab et al. | 606/41 |
| 2006/0015261 A1* | 1/2006 | Mann et al. | 702/19 |
| 2006/0017563 A1* | 1/2006 | Rosenfeld et al. | 340/539.12 |
| 2006/0084070 A1* | 4/2006 | Rieder et al. | 435/6 |
| 2006/0166239 A1* | 7/2006 | Chen et al. | 435/6 |
| 2006/0280786 A1* | 12/2006 | Rabinow et al. | 424/450 |
| 2007/0003931 A1* | 1/2007 | Mrazek et al. | 435/6 |
| 2007/0077610 A1* | 4/2007 | Ghai et al. | 435/13 |
| 2008/0311040 A1* | 12/2008 | Berry et al. | 424/9.1 |
| 2009/0087856 A1* | 4/2009 | Caldwell et al. | 435/6 |
| 2009/0138286 A1* | 5/2009 | Linder et al. | 705/3 |
| 2009/0216561 A1 | 8/2009 | Woo | |

FOREIGN PATENT DOCUMENTS

| | | |
|---|---|---|
| WO | 2004/003550 | 1/2004 |
| WO | 2006/044686 | 4/2006 |
| WO | 2007143617 | 12/2007 |

* cited by examiner

METHODS AND SYSTEMS FOR IMPROVED PHARMACEUTICAL INTERVENTION IN COAGULATION CONTROL

This application claims priority to our U.S. provisional application with the Ser. No. 61/106695, which was filed Oct. 20, 2008, and which is incorporated by reference herein. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is regulation of blood coagulation using coagulants and anti-coagulants, especially as it relates to administration of warfarin and Vitamin K.

BACKGROUND OF THE INVENTION

Warfarin and various other Vitamin K-inhibiting medications (collectively known as coumarins; the terms coumarin(s) and warfarin are used interchangeably herein) are widely used anticoagulants and act by inhibiting the Vitamin K-associated carboxylation of coagulation factors II (prothrombin), VII, IX and X, as well as proteins S & C. Reduced clotting is indicated for patients with atrial fibrillation, heart valve implants, venous thromboembolism and other conditions, and an estimated 3 million people take coumarins in the US. Warfarin inhibits the enzyme vitamin KO reductase, which reduces the oxidized vitamin K epoxide (KO) to Vitamin K1 that is in turn reduced to vitamin KH2 by the warfarin-resistant vitamin K reductase. Vitamin KH2 is then available for carboxylation of glutamic acid residues in several proteins, including several coagulation factors. In the process, KH2 is oxidized to the epoxide. Therefore, it is noted that warfarin only affects the recycling of vitamin K and that its inhibition of Vitamin K metabolism can be overwhelmed by an increased intake of Vitamin K.

The coagulation cascade itself is measured as the PT or "Prothrombin time," the time taken for plasma to clot following the addition of thromboplastin. Typically PT is expressed in terms of the INR, the International Normalized Ratio, which is used to standardize anticoagulant measurement between laboratories to account for reagent and process specific variations. INR is defined as:

$$INR = (PTpt/PTnorm)^{ISI}$$

where PTpt is the patient's prothrombin time measured in seconds, PTnorm is the prothrombin time for a pool of normal, untreated plasma, and ISI (International Sensitivity Index) characterizes the reactivity of the thromboplastin. An elevated INR (above a range of about 0.8 to 1.3) reflects a prolonged PT or slowed clot formation, which is the basis of warfarin's utility as a medicine. The therapy is usually geared to achieve a target INR range, typically $2.0 \leq INR \leq 3.0$. Lower intensity anti-coagulation, with $1.5 \leq INR \leq 2.5$ has been shown effective against deep vein thrombosis, accompanied by a reduction in bleeding complications, while higher intensity anti-coagulation, target range $2.5 \leq INR \leq 4.5$, has been used with heart valve replacement.

Warfarin therapy results in a gradual lowering of the pool of clotting factors, based on their degradation in the body as fewer factors are produced. A loading dose of warfarin is not recommended since, although it lowers the prothrombin time more quickly, the high initial dose can lead to rapid depletion of Protein C, a short-lived clotting factor, and to excessive anti-coagulation. Bleeding is the primary danger of warfarin treatment, as detailed in an ongoing series of conference reports from the American Conference of Chest Physicians. Major bleeding occurs at a rate of 0.8%-2.0% per year in patients on warfarin, depending on the primary indication; this compares to a risk of serious thromboembolism in untreated patients with a first diagnosis of 7% per year. Fatality rates for patients on warfarin are on the order of 0.18% for extended therapy (over 6 months). The ACCP report emphasizes the result of variations in anti-coagulation as follows:

"... Increased variation in the anticoagulant effect, manifested by variation in the INR, is associated with an increased frequency of hemorrhage independent of the mean INR. This effect is probably attributable to the increased frequency and degree of marked elevations in the INR. Approaches to improve anticoagulant control (minimize INR fluctuations) could improve the safety and effectiveness of vitamin K antagonists..."

The state of the art in anti-coagulation control is the skilled physician interpreting a series of INR measurements in the patient, and deciding whether to increase, leave unchanged, or lower the dose based on the last measurement. The second decision is then to fix the date of the next measurement, based on whether the current measurement was satisfactory, or to monitor the results of any changes in dose. When the INR is dangerously high, a physician may withhold doses of warfarin or prescribe one or more doses of Vitamin K to counteract the excess warfarin and to so lower the INR quickly, or to withhold warfarin and dose with Vitamin K.

Most physicians operate under a set of assumptions about warfarin, which is reflected in numerous reviews, published dosing algorithms and analysis of computer programs intending to replace subjective judgment of a physician. These key assumptions are as follows:

a. Warfarin takes time to act, but the effect of previous doses on the INR diminishes quickly with time.

b. The effect of warfarin is to inhibit the production of clotting factors. However, it should be noted that there are few studies on the quantitative relationship between Prothrombin Complex Activity and the INR, and that the time-course of the inhibition is poorly characterized.

c. The patient's sensitivity to warfarin changes fairly rapidly, making changing of the dose of warfarin an appropriate step where INR is high or low. Thus, withholding warfarin will bring down a high INR sufficiently quickly that it is preferred as an intervention. Lowering the warfarin dosage should lower the INR fairly quickly, so that if an INR remains high after a few days of the new lowered dosage, a further lowering is recommended.

d. The effects of a dose of Vitamin K are quick but transitory.

For example, the recently published computer model ICAD reflects these assumptions and is unable to improve coagulation control in the clinic, even compared to the earlier and more primitive computer model TRODIS. In a clinical trial comparing these programs, 712 patients were randomized to either program and followed for a year with 12,000 INR tests. Patients on both programs were within a broad therapeutic range 80% of the time, which is consistent with a distribution of the INR typical of patients managed without advice from the computer models. Clearly, neither algorithm reduced INR variation. Moreover, as was shown in this study, patients spent 4% of their time with a low INR excursion and 16% of their time with a high INR excursion, indicating that the dosage of anti-coagulant was consistently too high. Both algorithms presented a suggested new dose to the attending physician as their primary output, which were rejected by the physician 20% of the time for ICAD and 9% of the time for TRODIS. However, TRODIS failed to make a suggestion and demanded physician input at 39% of visits, versus only 2% of visits for ICAD.

Such and other case studies strongly suggest that the above assumptions fail to properly reflect the pharmacokinetics of the coumarins and other factors. Moreover, as these assumptions also guide most practitioners in their treatment of patients, significant improvements are still to be realized.

In other known methods as described, e.g., in U.S. Pat. App. No. 2009/0216561, a patient's INR, a target INR, and prior cumulative dosage of anticoagulant during a treatment period is used to calculate a new dosage of anticoagulant for the next treatment period. While such method is conceptually simple and potentially reduces the frequency of over- and under-dosages, adjustment to a desired INR is typically slow. Moreover, accuracy may be less than desirable at higher INR values. In a further known method, as described in WO 2004/003550, metabolic phenotyping is used in INR maintenance. Such method provides new aspects of control, however, is typically unsuitable for initiation therapy and reduction of large INR variations. Alternatively, individualized coagulant dosages can be determined on the basis of polymorphisms in the VKORC1 gene, which is responsible for metabolizing warfarin as taught in WO 2006/044686. Additional analysis of CYP2C9 may further improve proper dosage prediction as disclosed in WO 2007/143617. While these methods tend to identify individual variations in warfarin metabolism, they nevertheless fail to reduce variability in INR, especially where the INR is relatively high.

Consequently, while many methods and devices are known to control INR, all or almost all of them suffer from one or more disadvantages. Thus, there is still a need to improve systems and methods of pharmaceutical intervention in coagulation control.

SUMMARY OF THE INVENTION

The inventors have now discovered a dose-response relationship for Vitamin K antagonists, as well as for Vitamin K itself in the anti-coagulated patient, which can be numerically expressed to so form a basis for computation of appropriate initial and ongoing dosing, and even early detection of non-optimal dosing.

More particularly, the inventors discovered quantitative dose-response relationship in the anti-coagulated patient in which INR is a function of dosage with Vitamin K antagonists (coumarins) and Vitamin K. Remarkably, and when expressed in graphical form, this dose-response relationship has a shape that is opposite to conventional dose-response curves. Most typically, the dose-response curve according to the inventive subject matter is fitted to the patient's own INR data by convolution of his historical dosage data for estimation of patient-specific parameters, which are then used to calculate an optimum dose of Vitamin K antagonists for that patient.

It should be appreciated that the so calculated optimum dose can be relatively closely approximated by alternating available dosage forms to yield an average weekly dose that will approach the calculated optimum. Moreover, the algorithm can be used to predict the effect of supplemental Vitamin K on the anti-coagulation status to speed adjustment of the response or to stabilize the response. As the quantitative dose-response relationship can be expressed in a mathematical model, computer programs and other technical implements can be used to provide guidance for a physician. In further contemplated aspects of the inventive subject matter, methods are presented for computing a patient's unique half-time for attaining a stable effect and for predicting the INR during the transition to stability. Additionally, related devices to control the appropriate dosage for the patient by high-frequency dose oscillation (e.g., daily adjustment) are disclosed.

Based on the above and additional findings, the inventors therefore contemplate a method of assisting anticoagulant therapy in a patient in which a coagulation calculator is provided that is configured to perform a calculation operation where logit (1/INR)=–log (INR–1) is used as a dependent variable and to so produce a result based on the calculation operation. The coagulation calculator is further preferably configured to allow presentation of a result of the calculation operation.

In especially preferred aspects, the calculation operation is a calculation of a target dosage of an anticoagulant to achieve a desired INR value, wherein the target dosage of the anticoagulant is calculated according to equation (I)

$$\log (INR-1) = \log (I^*-1) + b(w-w^*) \quad (I)$$

wherein INR is the INR measured in the patient, $I^*$ is the desired INR for the patient, b is a patient-specific response to the anticoagulant (i.e., a patient-specific parameter which gives the slope of the dose-response curve at the optimum dose), $w^*$ is the target dosage, and w is the effective dose of the anticoagulant. Alternatively, where vitamin K data are available or needed to compute the correct dosage, the target dosage of the anticoagulant is calculated according to equation (II)

$$\log (INR-1) = \log (I^*-1) + b(w-w^*) - c \log (K/K0) \quad (II)$$

wherein INR is the INR measured in the patient, $I^*$ is the desired INR for the patient, b is a patient-specific response to the anticoagulant (i.e., a patient-specific parameter which gives the slope of the dose-response curve at the optimum dose), $w^*$ is the target dosage, w is the effective dose of the anticoagulant, c is a patient-specific parameter, K is effective uptake of Vitamin K by the patient, and K0 is average uptake of Vitamin K by the patient. Moreover, where supplemental vitamin K uptake, rK0, is required, the dosage for the uptake may be calculated according to equation (III)

$$r = \exp[b(w1-w^*)/c] - 1 \quad (III)$$

wherein w1 is an anticoagulant dosage that is greater than the target dosage, and wherein the remaining parameters are as defined above.

For initiation of anticoagulant therapy of a patient, the target dosage of the anticoagulant is calculated according to equation (IV)

$$w^* = w - (1/b) \log [(INR-1)/(I^*-1)] \quad (IV)$$

wherein INR is a first INR value measured in the patient, $I^*$ is the desired INR for the patient, b is an a priori value of sensitivity to the anticoagulant applicable to the patient's known characteristics, wherein $w^*$ is the target dosage, and wherein w is an effective dose based on an a priori value of half-stabilization time applicable to the patient's known characteristics. The a priori values of b and the half-stabilization time are replaced by patient-specific estimates as sufficient INR data are obtained.

Viewed from a different perspective, a coagulation calculator is contemplated that includes a memory element functionally coupled to a processor, an input module, and an output module, wherein the memory element stores software instructions to perform a calculation operation in which logit (1/INR)=−log (INR−1) is used as a dependent variable, wherein the processor is configured to execute the software instructions to so produce a result, and wherein the output module is configured to allow presentation of the result. With respect to specific equations and uses, the same considerations and formulae as provided above apply.

Various objects, features, aspects and advantages of the present invention will become more apparent from the following detailed description of preferred embodiments of the invention.

DETAILED DESCRIPTION

Figure 1:
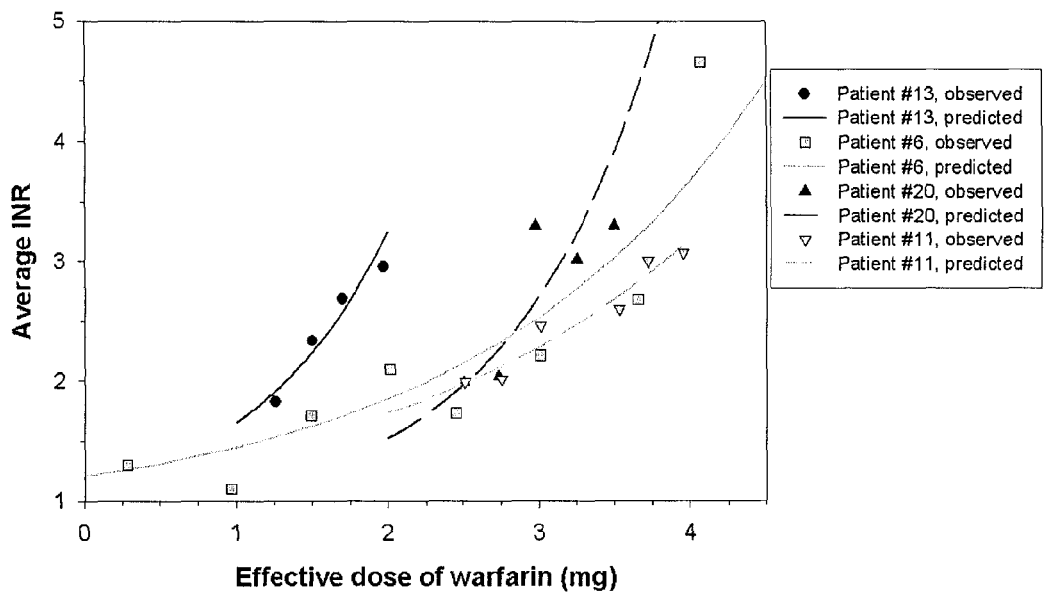
FIG. 1 is a graph illustrating the dose-effect relation for patients receiving a low average daily dose of warfarin.

The inventors have now discovered a significantly improved and quantifiable dose-response relationship for Vitamin K antagonists for use in coagulation control, which allows to establish a more constant dosage of required medication and to develop/take into account patient-specific sensitivity to warfarin and Vitamin K. Contrary to established assumptions and calculations, the inventors discovered that the most accurate dependent variable is logit (1/INR)=−log (INR−1).

It should be appreciated that the use of the logit form of the dependent variable has heretofore not been recognized. On the contrary, previous calculations have used the log of the ratio of (INR(predicted)−1) to INR (measured)−1) as a minimization criteria in the algorithm since it was assumed that INR by definition would be the ratio between two quantities and would have a theoretical lower bound of 1. Such assumption failed to use this construction as the dependent variable in the algorithm and failed to appreciate the effect of the transformation on stabilizing the variance. Using logit (1/INR) as the dependent variable stabilizes the variance across all values of INR as shown below and further simplifies the relation between INR and dose of either coumarins or their antagonist Vitamin K and so also reduces the number of parameters to be estimated for each patient. Unless specified otherwise, the term "log" as used herein refers to the natural logarithm (having the constant e for the base of the logarithm).

In typical examples, log (INR−h) is used with 0<h<1 (most typically, h is about 0.85) as measurements of INR=1 occur, which would provide a log of negative infinity, and as the "normal" INR is unity only on average, since the standard deviation of INR is small but not precisely zero for "normal" patients. Thus, it should be noted that the choice of h=0.85 is used as a practical value that suits most cases. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

The effect of Vitamin K antagonists provides an increased clotting time, as expressed by the measured INR, via reduction in the clotting factor concentration. The INR is dose-responsive to the clotting factors, with the reciprocal of the INR approaching 1 asymptotically as the clotting factors increase in concentration. Consequently, logit (1/INR) can be expressed as:

Logit (1/*INR*)=*y* log (*PCA*)−*x* where PCA or Prothrombin Complex Activity is the "concentration" of the clotting factors, and x and y are parameters. This relation can be derived from the mass-action interaction of Vitamin K and coagulation factors, and the inhibition of the KO reductase.

In the following, warfarin is used as a model Vitamin K antagonist. Based on the above, it can now be shown that the quantitative depletion of the clotting factors can be efficiently represented by the amount bw, where w is the effective dose of the particular antagonist (here: the daily warfarin dosage in milligrams), and b is a measure of the patient's sensitivity to the antagonist or the slope of the dose-response curve at the dose w (this approach assumes a linear metric for depletion, however, a logarithmic relation is also contemplated):

Logit (1/*INR*)=*y* log (*PCAo*)−[*x*+*bw*]; and logit (1/*INR*)=−log (*INR*−1).

Hence:

Log (*INR*−1)=[*bw*+*x*]−*y* log (*PCAo*)

To simplify, a=y log (PCAo)−x, which expresses the fixed contribution of the patient's own clotting factor system; this will result in equation (1)

$$\text{Log }(INR-1)=bw-a \tag{1}$$

Consequently, the patient-specific parameters are now a and b. It should be noted that b is a characteristic of the patient's direct response to warfarin and generally does not vary with time, except slightly with age. In the absence of further information, a is assumed to be a constant characteristic of the patient, but as will be shown below, also includes the effects of the intake of Vitamin K on the patient's INR, whose effects can be represented by adding another term (see below). It should be pointed out that Equation (1) is a proposition, not a definition, because it specifies what value of the INR will be observed, given values for a, b and w. Furthermore, it should be appreciated that the value predicted for a particular patient thus depends only on w regardless of when in the treatment sequence it occurred. Therefore the physician can use a graph of a patient-specific dose-response curve with some assurance that it will continue to be applicable, unless the patient's Vitamin K intake changes significantly. The mean value of a in equation (1) is about 2.8 and the mean value of b is about 0.54 for the patients studied, all of whom were taking warfarin as Vitamin K antagonists. These two parameters relating INR to effective dose w can be seen as the scale factor for the dose a and the steepness of the dose response b.

Figure 2:
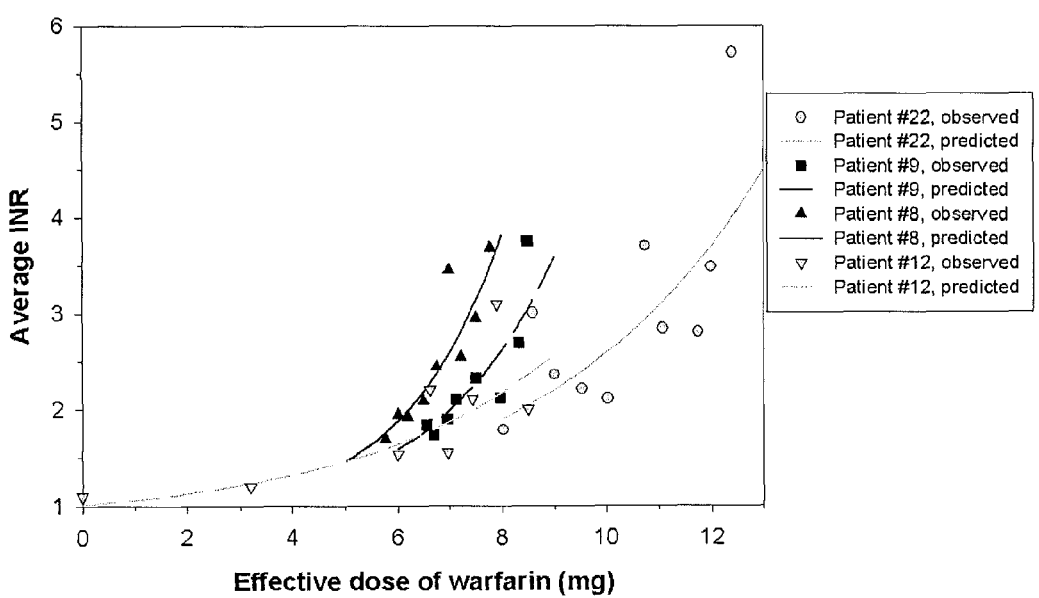
FIG. 2 is a graph illustrating the dose-effect relation for patients receiving a high average daily dose of warfarin.
Figure 3:
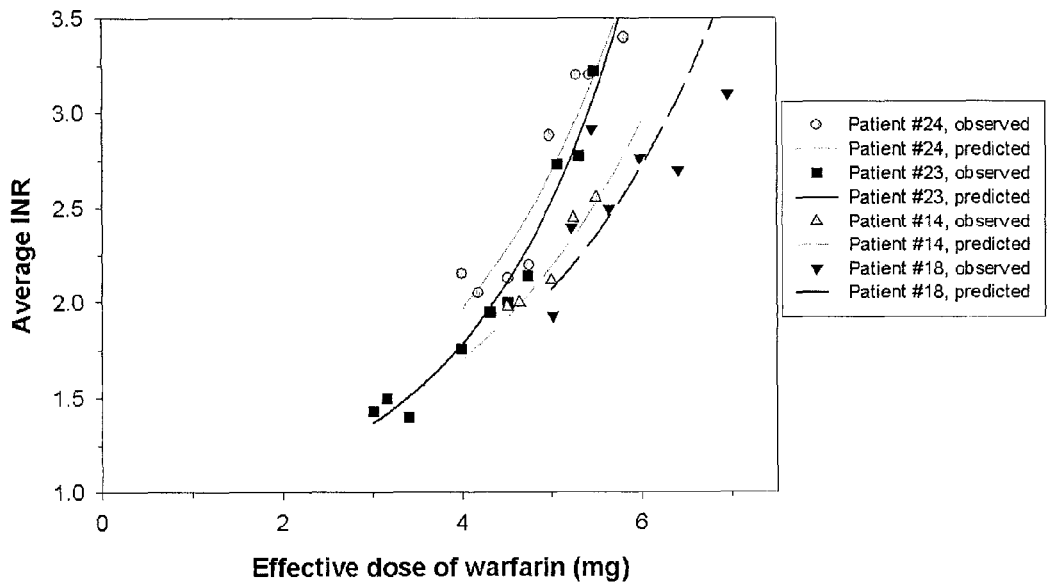
FIG. 3 is a graph illustrating the dose-effect relation for patients receiving a medium average daily dose of warfarin.

FIGS. 1, 2 and 3 display the dose-effect relations revealed when equation (1) was fitted to the measured INR of actual patients, who sometimes were given single doses of Vitamin K. The therapeutic range was 2.0 to 3.0 for every patient. The patients in FIG. 1 required a low average daily dose of warfarin, Patient #6 having received 5 mg oral Vitamin K on two occasions. The patients in FIG. 2 required a high average daily dose of warfarin, Patient #12 having received 5 mg oral Vitamin K on one occasion. The patients in FIG. 3 required a medium average daily dose of warfarin, Patient #18 having received 5 mg oral Vitamin K on one occasion. The difference between the figures in the dose scale shows the effect of the parameter a in equation (1).

Based on the above, it should be recognized that when I* is the target value at which the INR should be maintained, the optimum dose w* should be maintained according to equation (2)

$$w^* = (1/b) \cdot [a + \log(I^* - 1)] \quad (2)$$

This optimum dose w* is the maintained dose which will keep the patient's INR closest to the target I*.

The parameter a, derived as a function of w* from (2), can now be replaced in equation (1) to yield the core equation (3) according to the inventive subject matter:

$$\log(INR - 1) = \log(I^* - 1) + b(w - w^*) \quad (3)$$

The target INR, I*, is specified by the physician in accordance with the patient's medical history (typically I*=2.5, the midpoint of the usual therapeutic range). Since the optimum dose, w*, is what the physician wants to know, equation (3) will be the most practical used in routine clinical applications. The two patient-specific parameters b and w* are estimated by standard methods, such as maximum likelihood or least squares.

It should be especially appreciated that expressing the dose relationship in the form of the equation (3) has several important advantages: (a) The patient's data will typically be within available and common values as the physician is trying to locate w*. Good estimates of the parameters can thus be obtained quickly. (b) Rough, but clinically useful estimates of w* can be made even with crude methods applied to very limited data. Even one INR and one effective dose w (see below) can be substituted into (3) to yield a first estimate of w*.

For example, the optimum dose, w*, can be estimated from the first INR following the initiation of warfarin therapy. From equation (3):

$$w^* = w - (1/b) \log[(INR - 1)/(I^* - 1)]$$

The effective dose, w, can be estimated by assuming that the patient has the population average half-maximal time. The optimum dose, w*, can then be estimated from the above equation by assuming that the patient has the population average sensitivity, b. This method yields an estimated optimum dose of only 1.88 mg/day, after three days of therapy and an INR of 1.5, for the unusually difficult patient of Grice et al. (J. Thromb. Haemost. 2008; 6: 207-9) whose maintenance dose they ultimately estimated to be 0.9 mg/day. Such estimates, if sufficiently accurate, will prevent dangerous over-anticoagulation of the patient during this phase of treatment. The inventors envisage a stepwise transition to the fully-estimated model, as INR data accumulate, by methods known to those skilled in the art, such as likelihood ratio or minimum error. They also envisage that the a priori assumptions about sensitivity and half-maximal time will be improved by taking account of the patient's genetic profile and other personal circumstances.

Figure 4:
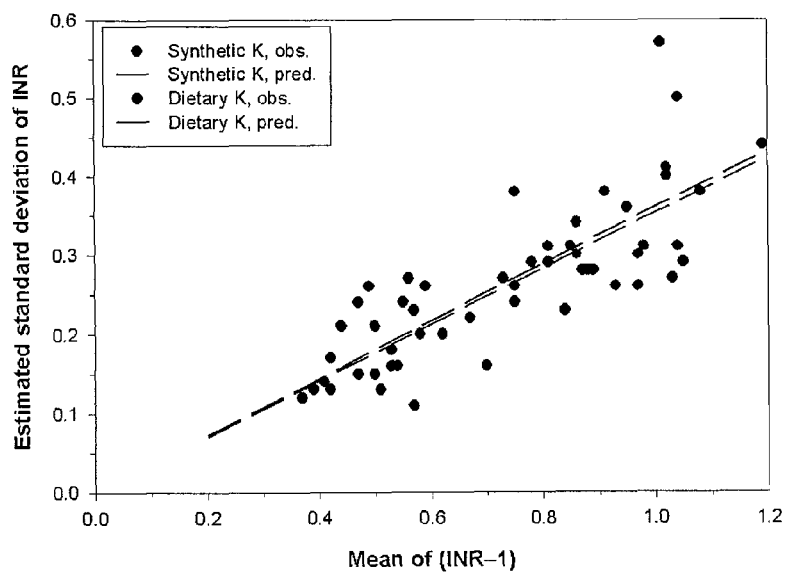
FIG. 4 is a graph illustrating estimated standard deviation of INR as a function of the mean of (INR−1).

With respect to the variation of INR and implications for management of anti-coagulated patients, several observations should be noted. As shown in FIG. 4, the standard deviation of the INR is proportional to the mean of INR−1, which has to the best of the inventors' knowledge not been appreciated in the art. Here, the data were obtained from Tables 3 and 4 of Schurgers et al. (Blood. 2004 Nov. 1; 104(9):2682-9). As can be readily seen, the standard deviation of INR is proportional to mean (INR−1). The dashed lines are fitted functions of proportionality. Thus, it can be taken that the Coefficient of Variation is constant across the measured data, from low to high values. It is also well known that a logarithmic transformation of such data yields a constant standard deviation. Consequently the standard deviation of log (INR−1) will be independent of its mean, and the general stability of the patient's INR can be properly measured by the standard deviation of the residual variation from the values predicted by equation (3). Unaware of the relation in FIG. 4, previous work has measured stability by the standard deviation of the untransformed INR, thus confounding it with its level. Thus a recent study concluded that adding exogenous Vitamin K to the patients' warfarin dosage had a general systemic effect of reducing the variation in their INR measures, when the exogenous Vitamin K simply lowered the INR and therefore its variance.

Any history of INR long enough to permit an accurate estimation of the standard deviation will usually include some adjustments to the dose as the physician treats symptoms of over- and under-anticoagulation. The effect of these varying doses can be discounted using the Equation (3), but, with no dose-response function available, previous work had no choice but to include the variation in INR from changing doses when computing the standard deviation. Thus, this measure of the patient's stability has had to include variation attributable to the physician. The dose-response relation presented here enables measuring the true stability of the INR, which is clinically of considerable importance for the reasons already given.

With respect to the half-time to stabilization the following should be noted: Warfarin requires time for its effect to stabilize. The clotting factors have to be depleted, or in the case of a reduction of dose, the excess warfarin in the system must be metabolized, while the pool of clotting factors increases slowly in the presence of the remaining warfarin. In the present invention, an empirical approximation is used to predict the time course of the patient's response to a change in a dose. Here, the "effective dose" is defined as that steady dose whose effect on the INR is equivalent to the amount of warfarin in the system at a particular time. In the case of a patient taking the same dose for an extended time, the "effective dose" equals that regular dose after the stabilization time. The "effective dose" only needs to be calculated when there is a change in dosage and during the stabilization period.

Figure 5:
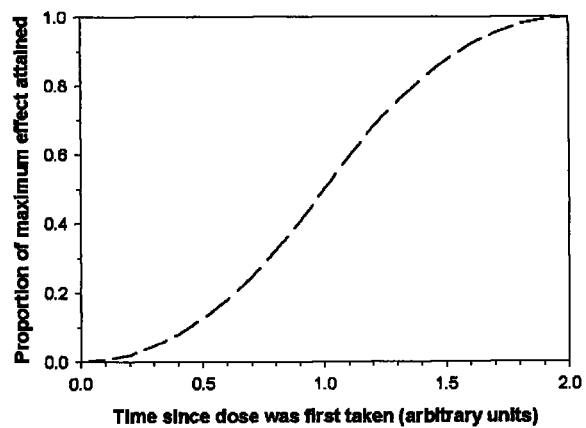
FIG. 5 is a graph depicting the effectiveness of a maintained dose of warfarin as a function of time since the dose was taken.

The "effective dose" is calculated by convolving the actual dose with a function of time since the dose was taken. This function represents the effect of a single dose on the INR through time. A first approximation to the convolution for calculating the "effective" dose for warfarin is disclosed here. It is assumed that the weighting for a dose taken just once is a triangular function with a slope of k from the time the dose is taken to the time of its maximum effect on INR, followed by a tailing off with a slope of −k. The resulting function for a maintained daily dose is an S-shaped growth function, consisting of two quarter-parabolae, depicted in FIG. 5. More specifically, the graph of FIG. 5 illustrates the effectiveness of a maintained dose of warfarin as a function of time since the dose was taken using the assumption that a single dose has an effect that can be graphed as a triangular profile over time. Here, the half-maximal delay is one unit of time at which the dose has half its maximum effect. When the patient stops taking the drug, the decay is reversed. This approach is consistent with the general shape of the time-course of PT following a single dose of warfarin, with or without Vitamin K.

Using the dose response equation (1), the inventors found correlations on the order of 0.6 between the effective dose and the corresponding observed value of log (INR−1). The approximation of the convolution disclosed here may be extended to other weightings using tools commonly known in the art. Consequently, it should be appreciated that any convolution function that yields an approximation of the effective dose (such that the effect of a new dose accelerates and then decelerates over the interval to exhibit a roughly sigmoid effect on INR over the time interval) is expressly contemplated herein. In contrast, heretofore known methods assumed that the effect of a dose of warfarin is proportional to the plasma concentration of that dose (i.e. maximal on the day it is taken and then declining exponentially with time). The importance of a delayed effect of the dose for predicting the INR can be seen in FIGS. 6-8, where the physician's out-of-phase changes to the dose induce corresponding oscillations in the INR some days later.

Figure 6:
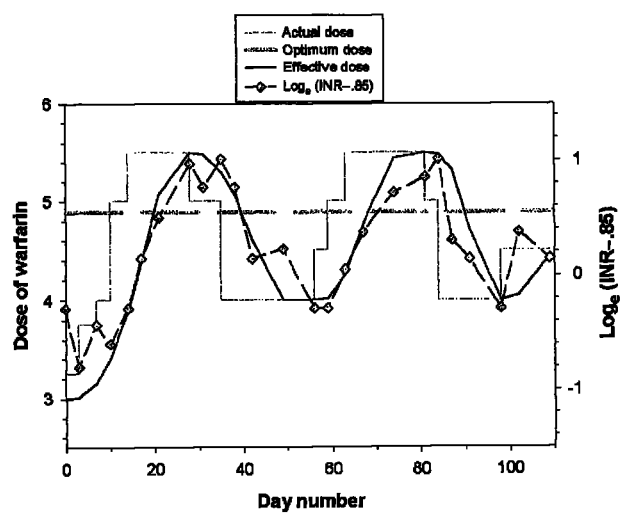
FIG. 6 is a graph depicting actual, effective, and optimum doses for one exemplary patient.
Figure 7:
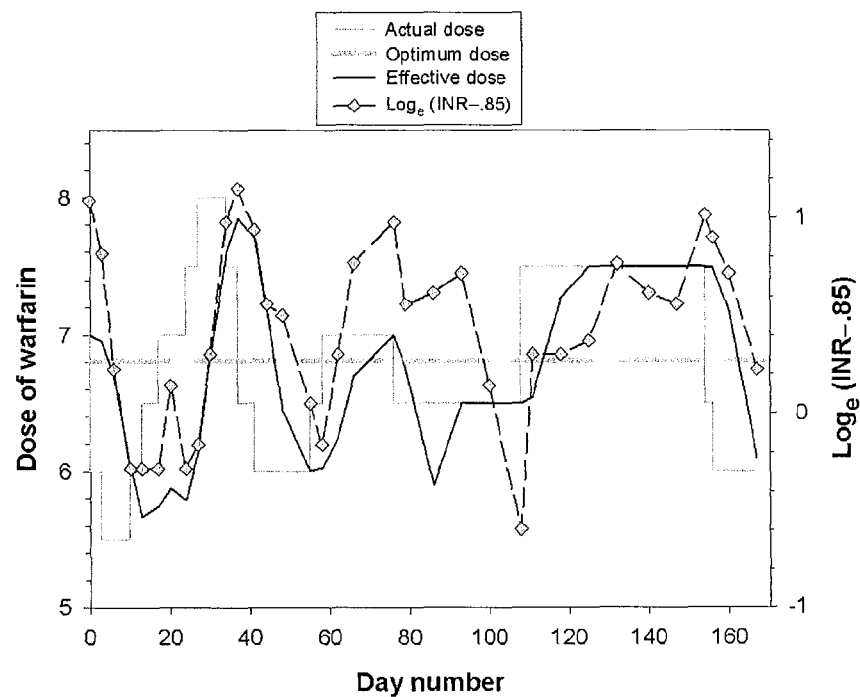
FIG. 7 is a graph depicting actual, effective, and optimum doses for another exemplary patient.
Figure 8:
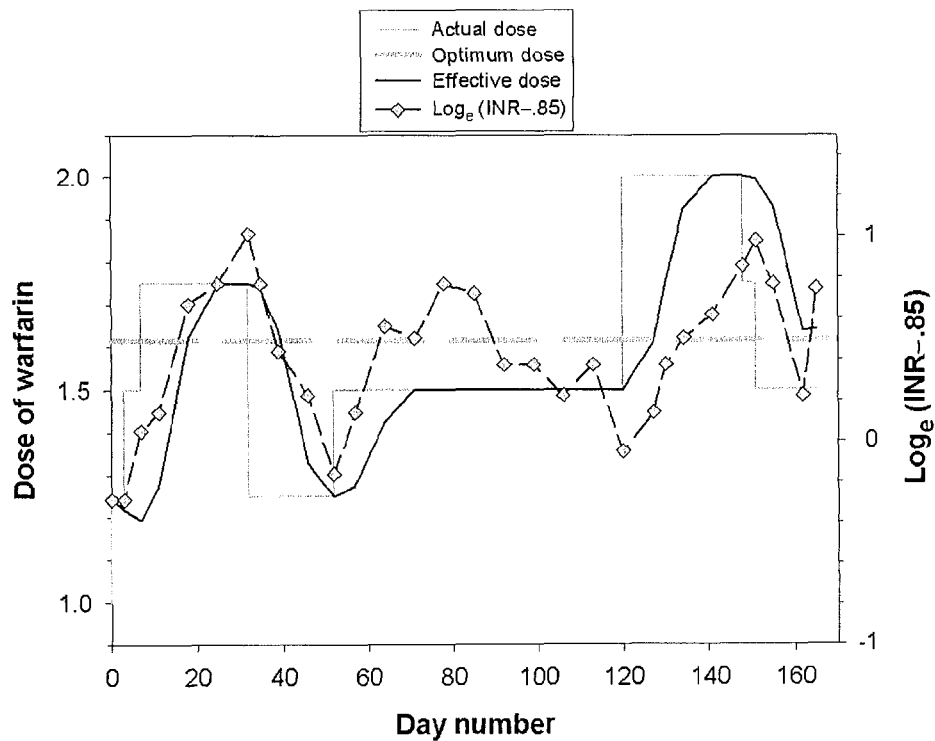
FIG. 8 is a graph depicting actual, effective, and optimum doses for yet another exemplary patient.

FIGS. 6, 7 and 8 each show a graph of actual, effective, and optimum doses for an exemplary patient. The "optimum" dose is the dose expected to yield an INR at the mid-point of the therapeutic range. The effective doses were calculated using a half-maximal delay of 6.4, 6.4 and 9.0 days respectively. The correlation of log (INR−~0.85) with the effective dose is 0.91, 0.75 and 0.75 respectively. The patient in FIG. 7 missed his dose on days 18 and 77.

The parameter $t_{max}\frac{1}{2}$ used for this convolution is the time to attain the half-maximal effect for a maintained dose, which is also the time to attain the maximum effect of a single dose. The parameter $t_{max}\frac{1}{2}$ can be estimated by standard non-linear methods, at present by minimizing the residual sum of squared deviations between the observed and predicted values of log (INR−1). A general average value of $t_{max}\frac{1}{2}$ for warfarin is computed to be 6.4 days, but will vary from patient to patient and thus needs to be fitted to the individual patient data. Therefore, the time until the INR has stabilized on a constant dose is usually 13 days for warfarin. However, it should be noted that many people carry variant genes for the primary enzyme CYP2C9, which affect the rate of metabolism of Vitamin K antagonists and so leads to considerable variations in half-time parameters among patients.

It is therefore envisioned to use these data to estimate for each individual the time to half-maximal effect of the dose, the relevant portion of the dose-response curve, and the residual standard deviation of the patient's log (INR−1) from their previous history of dose and measured INR. Warfarin therapy is usually long-term. Therefore, many patients have an extensive history of response to the drug. These computed parameters can be used to predict the effect of a change in the dose, to detect a shift in the patient's response, and to assess whether a new INR is truly beyond acceptable bounds or represents a random variation within them. By contrast, known methods typically fail to allow computation of individual half-maximal times, to depict the relevant portion of the dose-response curve, and to evaluate the degree of variation in the patients' INR due to changes of dose versus random fluctuation.

As already pointed out above, even where a patient's data are not extensive enough to obtain a good estimate of his half-maximal time, clinically useful estimates of the patient's optimum dose can still be obtained by assuming that the estimate is the same as the general average. As data accumulate with time, the new data can be used to improve this estimate.

Moreover, it should be appreciated that the system and methods presented herein also allow for computation of the effect of Vitamin K to adjust the effective dosage. Vitamin K is used as an antidote to over-dosage of Vitamin K antagonists, either by injection or oral tablet. Use of Vitamin K brings the INR into range faster than cessation of Vitamin K antagonists, which must still be metabolized before the pool of clotting factors can be increased to lower INR. A patient presenting with an excessive INR who is not overdosing on warfarin is typically Vitamin K deficient, presumably due to reduced intake of Vitamin-K-containing foods, but also possibly due to interaction with other medications. Accidental overdose is another possible route to excessive INR. In most cases, the attending physician will require a suggestion of the amount of Vitamin K which would reduce INR to the therapeutic range, but not below it. It should be appreciated that the algorithm according to the inventive subject matter can suggest such a dose or range of doses based on the patient's history to assist the judgment of the physician.

More specifically, the reciprocal of INR will be dose-responsive to Vitamin K in the normal manner, as discussed above, so that Logit (1/INR) will be linear in log (K), where K is the effective total intake of Vitamin K in μg/day. Data on the total intake of Vitamin K are very rarely available in the clinic, but it is practicable to investigate departures from the usual amount when occasion arises, such as when a supplement of Vitamin K is prescribed. Therefore log (K) is expressed as the sum of two terms: log (K)=log (K0)+log (K/K0), where K0 is the average daily intake of Vitamin K.

The dose-response curve described here includes the effect of exogenous Vitamin K by considering the parameter a in equation (1) to be the sum of two terms, a=a'+c log (K0), where a' is another constant and c is a patient-specific parameter, and by adding a term for the effect of departures from K0. Thus, it follows that $$\text{Log }(INR-1)=bw-a-c\log(K/K0) \quad (4)$$

The value of the optimum dose, w*, in equation (2) is therefore the dose that will yield the target INR provided that the patient has his usual intake of Vitamin K, defined as the patient-specific parameter K0.

It should be appreciated that one could assert on the basis of equation (4) that, for any fixed dose of warfarin (no matter how large), a corresponding dose of vitamin K could be found such that INR will approach 1.0. While equation (4) is mathematically consistent with such assertion, it should be noted that the proper dose of vitamin K would increase exponentially as the dose of warfarin increases since equation (4) links warfarin linearly with the log of K. In practice, such calculation would likely not bear out, or at least put a patient at significant risk.

To overcome such hypothetical limitation, it is contemplated that the term "bw" could be replaced with the term "log(1+bw)". In such scenario, where w is in the range of usual clinical doses, the result will be closely approximated by equation (4), rendering the modified formula almost indistinguishable from the formula in equation (4). Consequently, it should be noted that the terms "bw" and "log(1+bw)" can be used interchangeably herein (at least where dosages of w are within normal clinical range). However, under most circumstances, the term "bw" will be preferred as such term significantly simplifies routine clinical application.

Still further, it should be appreciated that when Vitamin K uptake is taken into account, equation (3) can be formulated as $$\text{Log }(INR-1)=\log{(I^*-1)}+b(w-w^*)-c\log{(K/K0)} \qquad (5)$$

The patient-specific parameter c is estimated by standard methods, such as maximum likelihood or least squares. The average value derived from the literature data is 0.43. Since K0 is difficult to determine, the physician may try supplements of Vitamin K in addition to warfarin to estimate the values of both c and K0 using equation (5). For example, it is assumed that a patient has an INR of 3.2 when maintained on the current dose of warfarin alone, that the INR is 2.65 after a week of 100 µg daily supplemental Vitamin K, and that the INR is 2.4 after a week with a 200 µg daily supplement. The difference in equation (5) between warfarin alone and the two supplements shows that c loge(1+100/K0)=0.288 and that c loge(1+200/K0)=0.452. Iterative methods give the solution that c=0.394 and K0=93.15 µg Vitamin K. Consequently a daily supplement of 153 µg should yield a target INR of 2.5 for this patient without changing the dose of warfarin.

The effective total daily intake of Vitamin K is calculated from the patient's history in the same manner as the effective dose of warfarin, except that the half-time to stabilization of Vitamin K1 is estimated to be about 1.6 days. Using the methods disclosed here, one can come to accurate assessment of the patient's K0 by measuring the INR following supplemental doses of Vitamin K.

Figure 9:
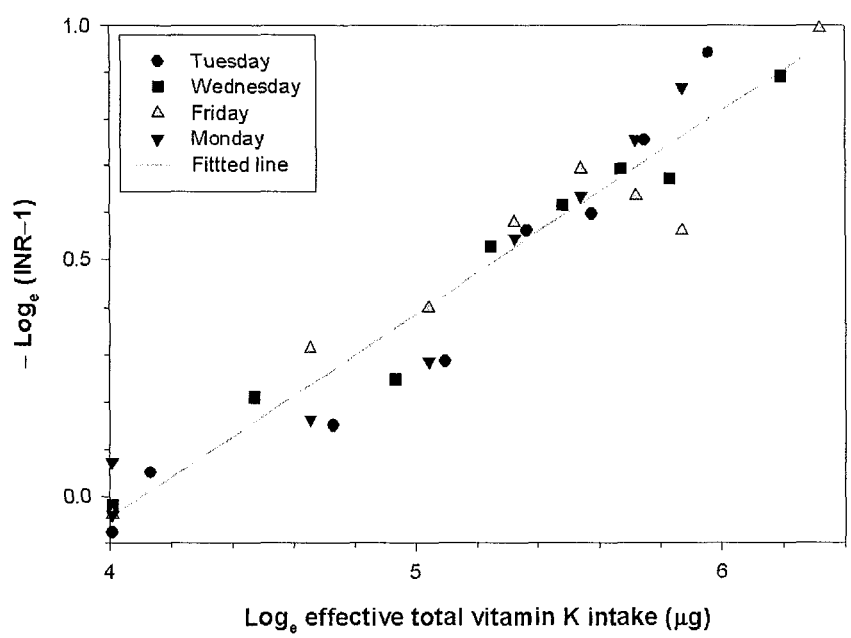
FIG. 9 is a graph depicting the effect of vitamin K intake on INR.

The parameters of this dose-response curve for Vitamin K are derived primarily from published data based on use of synthetic Vitamin K tablets. In such published studies, the average daily intake of Vitamin K was measured in the diet of the subjects at 55 µg. Here, we show the fit of equation (4) to these data in FIG. 9, which shows the measured INR (the effect) as a function of the total intake of Vitamin K (the dose) and is thus a true dose-response curve except that the INR is transformed in order to show that the data have the predicted linear relation. Here, vitamin K was obtained from a standard diet (approximately 55 mcg/day) supplemented by a daily dose of synthetic vitamin K. The dashed line is a fitted dose effect curve. Effective total vitamin K intake assumes that the effect of a dose is spread out over three days. The dose was increased each Monday before INR was measured; thus, the INR for Tuesday was one day after increase, etc.

The data available in the literature indicate that the standard deviation of the daily intake of Vitamin K is proportional to the mean intake, as might be expected. Consequently, the standard deviation of log (K) will be independent of K0. If K is an increase over K0 by a proportion r<1, so that K=(1+r) K0, equation (5) shows that there will be a decrease in log (INR−1) of about cr. This variation in log (INR−1) induced by the diurnal variation of intake will therefore be roughly constant in time and independent of the mean intake. A certain proportion of INR variation is thus due simply to random dietary factors and cannot be reduced without a diet where Vitamin K content is fixed.

Estimates of the average daily dietary intake of Vitamin K vary considerably according to the season, the geographical location, the method of estimation, and the characteristics of the individuals in question. The amount recommended in the USA for nutritional purposes is 90-120 µg/day. In Brazil the daily intake averaged over 3 days was reported to be 118 µg/day. In The Netherlands the average over 7 days was 54 µg/day, with a range of 32-101 µg/day. In Northern England the average for the 4 days preceding measurement of INR was 47 µg/day, with a range of 7-377 µg/day; but the average over 28 days was markedly higher at 76 µg/day, with a range of 18-211 µg/day. Note that the actual bioavailability of these intakes is a small fraction of that from synthetic Vitamin K.

Variation in Vitamin K intake can therefore be expected to have two distinct effects on the INR: (a) short-term fluctuations due to temporary departures from the mean intake, and (b) long-term trends as the mean intake drifts in response to such things as seasonal availability of dietary K. Here we also contemplate the routine use of Vitamin K to adjust the dosage of warfarin in order to permit the effective dose to approach the optimum dose more closely, especially in patients on low-dose warfarin, where the steps between dosage forms are large.

If $w1>w^*$ is the dosage form of warfarin chosen by the physician, then the target INR can be obtained with a supplemental daily amount, rK0, of Vitamin K such that:

$$r=\exp[b\,(w1-w^*)/c]-1 \qquad (6)$$

The combination of Vitamin K and Vitamin K antagonists was reported by Bertling et al in WO 01/37818A3 (Improved medication by simultaneous application of agonists and fixed dose antagonists). However, Bertling et al. failed to disclose or even suggest suitable methods of computing the relative dosage of agonist and antagonist, as is shown here. The amounts of Vitamin K administered are small and used simply to tweak the optimum dose to bring it closer to an available dosage form of warfarin. Quantities of less than 250 µg Vitamin K per day are sufficient.

Consequently, it should be appreciated that the dose-response relations presented herein may be employed to calculate the appropriate dosages in a patient. More specifically, the patient's own data can be used to compute the three parameters that characterize their response to warfarin: half-time to stabilization, and the two parameters of the dose-response curve w* and b. In difficult cases, the physician may wish to compute K0 and c as additional parameters by following the effects on INR of exogenous doses of Vitamin K.

The half-time to stabilization, or lag time, can only be estimated when the dose is varied in some particular wave form and the corresponding wave form can be located in the response. The input wave form must therefore have sufficient amplitude to reproduce itself in the output. In the majority of cases, when warfarin treatment is initiated in a patient for whom there is no history, the data will already be sufficient, as the physician must manipulate the dose in response to the first INR measurements. As already noted above, early, but often clinically useful estimates of the optimum dose can be obtained in practice by assuming that a new patient has the general average half-time to stabilization. Such estimates help to reduce the tendency of some physicians to make out-of-phase corrections to the dose. Very early estimates, based on the further assumption that the patient has the general average sensitivity to warfarin, have also been found to be useful. When the effect of the dose cannot be estimated from the patient's history, the physician should deliberately vary the dose systematically in order to obtain the parameters of the response. This method of deliberately introducing a transient over-dose and under-dose of anti-coagulants, using the induced variation to improve the fit of the dose-response parameters, and then using the dose-response algorithm to adjust the resulting INR into the therapeutic range is disclosed here. Once the lag-time and parameters of the dose-response function have been estimated, it should be appreciated that stabilization of the patient at the proper level is significantly easier.

Moreover, it is noted that transformation of the algorithms presented herein to an appropriate computer program, table, matrix, or other implement can be done using methods well known in the art. Most typically, a program or other tool will derive three parameters from the history of a patient's INR results and dosage. The program will then determine the optimal dosage for a targeted INR value, as well as predict the INR on successive days at the new dose, as the INR stabilizes at the new value. The program may also compute a combination optimum dose of warfarin and Vitamin K suitable to obtain the desired INR level, or alternatively, a series of standard dosage forms which average out to the optimum dose. Finally, in case of a high excursion of INR deemed threatening, for patients where K0 and c have been determined, and otherwise using the average values, the program can suggest a dose of VK sufficient to lower the INR safely to the target.

Thus, it is especially contemplated that a method of assisting anticoagulant therapy in a patient includes a step of providing a coagulation calculator and a further step of configuring the coagulation calculator to perform a calculation operation where logit (1/INR) =−log (INR−1) is used as a dependent variable and to produce a result based on the calculation operation. In yet another step, the coagulation calculator is configured to allow presentation of a result of the calculation operation. Consequently, and viewed from a different perspective, a coagulation calculator is contemplated that includes a memory element functionally coupled to a processor, an input module (e.g., keyboard, speech-to-text converter, mouse/screen in a graphical user interface, etc), and an output module (e.g., screen, printer, numeric/alphanumeric display, etc.), wherein the memory element stores software instructions to perform a calculation operation in which logit (1/INR)=−log (INR−1) is used as a dependent variable. Most typically, the processor is configured to execute the software instructions to so produce a result, wherein the output module is configured to allow presentation of the result.

It should further be appreciated that while the aspects of the inventive subject matter are discussed in the context of a coagulation calculator, various other computing devices including servers, interfaces, systems, databases, or other types of computing devices operating individually or collectively are also deemed appropriate. One should also appreciate the computing devices comprise a processor configured to execute software instructions stored on a computer readable storage medium (e.g., hard drive, RAM, flash, ROM, etc.). The software instructions preferably configure the computing device to provide the roles, responsibilities, or other functionality as discussed with respect to the specific apparatus. In especially preferred embodiments, the various servers, systems, databases, or interfaces exchange data using standardized protocols or algorithms possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network, portions of which may include wireless data transfer.

With respect to the interpretation of INR excursions, it should be noted that despite the accuracy of the disclosed function in explaining the variations in INR due to inappropriate dosing, there will still be unexplained residual variation in the INR. For example, the median correlation is r=0.69 between the calculated effective dose and the INR for the twelve patients in FIGS. 1 to 3, with a range of r=0.48 to r=0.91, depending on the patient's stability and the extent to which the physician manipulated the dose. Therefore, between 17% and 77% of the variance of the INR remains unexplained by the dose-response relationship alone. Using the patient's history and the log transform of INR−1, one can now compute a standard deviation for the patient and evaluate the probability of a high or low INR being significant, or simply occurring by chance. This is of some importance, since current algorithms for dosing regard all high or low excursions as potentially significant and recommend dose changes on INR results that may well be random.

It should further be appreciated that using the transformed standard deviation to evaluate the probability of an excursion being significant also balances the likelihoods for high and low excursions. Excursions below a targeted level of anticoagulation indicate the patient is in danger of clotting, but the low INR value also has a lower standard deviation. Therefore low excursions which appear modest are as likely as high excursions which appear dangerous on the untransformed scale. A patient with an average INR of 1.8 will be in the therapeutic range of 2.0 to 3.0 markedly less often than a patient with an average INR of 3.2. This is because the standard deviation at INR=1.8 is less than the standard deviation at INR=3.2. The patients of a physician who thinks that these INRs are an equivalent distance from the therapeutic range will be at greater risk of thromboembolism than of hemorrhage, when the point of the treatment is to balance these risks. That this is a real problem is confirmed by several papers which report that patients are more often below than above the therapeutic range, and the potential consequences are readily evident.

In practical application, the high or low measured INR can be assigned a probability based on the transformed standard deviation to inform the clinician. A percentage likelihood of the excursion being a random event, based on the previous history of the particular patient, will enable conservative reactions such as repeating the measurement at a later time, rather than an immediate dose change which can set off another round of oscillation. When an excursion is unlikely to be merely random, the physician will be reminded to inquire whether the patient has abided by the prescribed dosing regime during the previous week, to investigate drug interactions and whether the dietary intake of Vitamin K has deviated far from the normal amount in the previous two days.

Analysis of long-term patient data using the dose-response relation has revealed previously unreported cyclic variations in the parameter a and consequently also in w* that lead to rising and falling INR values over weeks and months. In some patients this cyclic variation may reach 20% of the average INR. There may be an annual component which follows the seasons, which may reflect the availability of Vitamin K-rich produce. The use of the algorithm in conjunction with regular testing of INR to detect and treat these cyclic variations by adjusting the dosage of either warfarin or Vitamin K or both is contemplated here.

In further contemplated aspects of the inventive subject matter, it should be appreciated that high frequency alternation may be employed to achieve the optimum dose. Often the optimal dosage will be an intermediate value which is not commercially available. For example, Coumadin-brand warfarin is available in 1, 2, 2.5, 3, 4, 5, 6, 7.5 and 10 mg scored tablets. The optimal dose calculated may be a fractional value not available by combining these dosage forms. In this instance, a good approximation of the optimal dose can be obtained by alternating the daily dosage. For example the average dosage of 1.25 mg/day can be obtained by taking three 1 mg and then a 2 mg in a repeating sequence. Other optimal dosages can be computed in the same manner Since the variation in dosage proposed has a much higher frequency than the oscillations seen above and the response requires 14 days to stabilize, no oscillation will be induced in the INR by such strategies. Since commercially available tablets will often not be close enough to the optimal dose, this high frequency method of dose adjustment can be used to provide an effective dose near the optimal one computed by the algorithm disclosed here. Therefore, devices to assist the patients in determining the appropriate tablet of this alternating series to take are contemplated, such as a programmable pill dispenser to dispense the appropriate pill in the sequence, or a programmable clock or a program for a computer or cell phone or PDA that performs the same function are all contemplated here. Even a pill box with sequential days adjusted to the optimum dose as an average will accomplish this purpose.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of predicting INR or a desirable dosage of a drug in anticoagulant therapy in a patient, comprising:
   providing a coagulation calculator;
   configuring the coagulation calculator to perform a calculation operation where logit $(1/INR) = -\log(INR-1)$ is used as a dependent variable and to produce a result based on the calculation operation;
   wherein INR is equal to $(PTpt/PTnorm)^{ISI}$, wherein PTpt is the patient's prothrombin time measured in seconds, PTnorm is the prothrombin time for a pool of normal, untreated plasma, and ISI characterizes a reactivity of a thromboplastin; and
   further configuring the coagulation calculator to allow presentation of a result of the calculation operation.

2. The method of claim 1 wherein the calculation operation is a calculation of a target dosage of an anticoagulant to achieve a desired INR value.

3. The method of claim 2 wherein the target dosage of the anticoagulant is calculated according to equation (I)

$$\log(INR-h) = \log(I^*-h) + b(w-w^*) \tag{I}$$

wherein INR is the INR measured in the patient, I* is the desired INR for the patient, b is a patient-specific constant that describes a patient specific response to the anticoagulant, w* is the target dosage, $0 < h < 1$, and w is the effective dose of the anticoagulant.

4. The method of claim 3 wherein the patient has been taking a same daily dose, w', of warfarin so long that the effective dose is equal to w'.

5. The method of claim 3 wherein w is estimated from the patient's dosage history.

6. The method of claim 3 wherein b is estimated from the values of w and the patient's corresponding INR.

7. The method of claim 2 wherein the target dosage of the anticoagulant is calculated according to equation (II)

$$\log(INR-h) = \log(I^*-h) + b(w-w^*) - c \log(K/KO) \tag{II}$$

wherein INR is the INR measured in the patient, I* is the desired INR for the patient, b is a patient-specific constant that describes a patient specific response to the anticoagulant, w* is the target dosage, $0 < h < 1$, w is the effective dose of the anticoagulant, c is a patient-specific parameter, K is effective uptake of Vitamin K by the patient, and KO is average uptake of Vitamin K by the patient.

8. The method of claim 7 further comprising a step of calculating a supplemental uptake of vitamin K to achieve a desired INR value.

9. The method of claim 8 wherein the supplemental uptake rK0 is calculated according to equation (III)

$$r = \exp[b(w1-w^*)/c] - 1 \tag{III}$$

wherein w1 is an anticoagulant dosage that is greater than the target dosage.

10. The method of claim 2 wherein anticoagulant therapy is initiated in the patient and wherein the calculation of the target dosage of the anticoagulant is calculated according to equation (IV)

$$w^* = w - (1/b) \log[(INR-h)/(I^*-h)] \tag{IV}$$

wherein INR is a first INR value measured in the patient, I* is the desired INR for the patient, b is an a priori value of sensitivity to the anticoagulant applicable to the patient's known characteristics, wherein $0 < h < 1$, wherein w* is the target dosage, and wherein w is an effective dose based on an a priori value of half-stabilization time applicable to the patient's known characteristics.

11. A coagulation calculator, comprising:
   a memory element functionally coupled to a processor, an input module, and an output module;
   wherein the memory element stores software instructions to perform a calculation operation in which logit $(1/INR) = -\log(INR-1)$ is used as a dependent variable;
   wherein the software instructions further allow prediction of INR or a desirable dosage of a drug in anticoagulant therapy in a patient using the calculation operation;
   wherein INR is equal to $(PTpt/PTnorm)^{ISI}$, wherein PTpt is the patient's prothrombin time measured in seconds, PTnorm is the prothrombin time for a pool of normal, untreated plasma, and ISI characterizes a reactivity of a thromboplastin;
   wherein the processor is configured to execute the software instructions to so produce a result; and
   wherein the output module is configured to allow presentation of the result.

12. The coagulation calculator of claim 11 wherein the calculation operation is a calculation of a target dosage of an anticoagulant to achieve a desired INR value.

13. The coagulation calculator of claim 12 wherein the target dosage of the anticoagulant is calculated according to equation (I)

$$\log(INR-h) = \log(I^*-h) + b(w-w^*) \tag{I}$$

wherein INR is the INR measured in the patient, I* is the desired INR for the patient, b is a patient-specific constant that describes a patient specific response to the anticoagulant, $0 < h < 1$, w* is the target dosage, and w is the effective dose of the anticoagulant.

14. The coagulation calculator of claim 12 wherein the target dosage of the anticoagulant is calculated according to equation (II)

$$\log(INR-h) = \log(I^*-h) + b(w-w^*) - c\log(K/KO) \quad \text{(II)}$$

wherein INR is the INR measured in the patient, $I^*$ is the desired INR for the patient, b is a patient-specific constant that describes a patient specific response to the anticoagulant, $0 < h < 1$, $w^*$ is the target dosage, w is the effective dose of the anticoagulant, c is a patient-specific parameter, K is effective uptake of Vitamin K by the patient, and KO is average uptake of Vitamin K by the patient.

15. The coagulation calculator of claim 12 wherein anticoagulant therapy is initiated in the patient and wherein the calculation of the target dosage of the anticoagulant is calculated according to equation (IV)

$$w^* = w - (1/b)\log[(INR-h)/(I^*-h)] \quad \text{(IV)}$$

wherein INR is a first INR value measured in the patient, $I^*$ is the desired INR for the patient, b is an a priori value of sensitivity to the anticoagulant applicable to the patient's known characteristics, $0 < h < 1$, wherein $w^*$ is the target dosage, and wherein w is an effective dose based on an a priori value of half-stabilization time applicable to the patient's known characteristics.

* * * * *